United States Patent
Green et al.

[11] 3,982,836
[45] Sept. 28, 1976

[54] METHOD AND MEANS FOR ENHANCING PRINTS FOR DIRECT COMPARISON

[75] Inventors: Harold Green, Los Angeles; Stephen J. Halasz, Claremont, both of Calif.

[73] Assignee: Harold Green, Los Angeles, Calif.

[22] Filed: Dec. 30, 1974

[21] Appl. No.: 537,112

Related U.S. Application Data

[63] Continuation-in-part of Ser. No. 468,425, May 9, 1974, Pat. No. 3,928,842.

[52] U.S. Cl. ............................ 356/119; 356/71; 356/165
[51] Int. Cl.² .................................... G01J 4/00
[58] Field of Search ............... 340/146.3 E, 146.3 F; 356/71, 118, 119, 165, 166, 168, 156

[56] References Cited
UNITED STATES PATENTS

| | | | |
|---|---|---|---|
| 3,200,701 | 8/1965 | White | 356/71 |
| 3,499,159 | 3/1970 | Carrier et al. | 356/119 |
| 3,532,426 | 10/1970 | Lemmond | 356/71 |
| 3,604,806 | 9/1971 | Redman | 356/71 |
| 3,619,060 | 11/1971 | Johnson | 356/71 |
| 3,790,286 | 2/1974 | Kraus | 356/118 |

*Primary Examiner*—John K. Corbin
*Assistant Examiner*—Richard A. Rosenberger
*Attorney, Agent, or Firm*—Robert Louis Finkel

[57] ABSTRACT

A method and apparatus for enhancing prints, such as fingerprints, for direct comparison. The method utilizes a transparent pressure-sensitive gel to capture a print pattern. A polarized beam of collimated light is passed through the gel. The pattern features impressed in the surface of the gel scatter light out of the optical path. The beam is then directed to a polarizing element oriented so as to filter out the scattered light rays and thereby produce a high-contrast image for direct viewing or further automated processing. In one embodiment of the apparatus single pressure-sensitive transparencies of individual prints are inserted in a polarized light path. In another, a film transport mechanism exposes successive regions of a strip of transparent pressure-sensitive film in a window for application of individual prints and advances the film to position each image imprinted on the film surface in the polarized light path. In both embodiments the modified light beam emitted by the transparency is projected through a polarization analyzer. A lens train further enhances the image by magnifying it and apodizing the enlargement.

12 Claims, 5 Drawing Figures

METHOD AND MEANS FOR ENHANCING PRINTS FOR DIRECT COMPARISON

BACKGROUND OF THE INVENTION

Related Application

This application is a continuation-in-part of our co-pending application Ser. No. 468,425, now U.S. Pat. No. 3,928,842, issued Dec. 23, 1975 for Fingerprint Comparator.

FIELD OF THE INVENTION

This invention relates generally to print or pattern comparators, and more particularly to methods and means such as those described in our aforementioned co-pending application for automatically comparing a pair of fingerprints by processing their superimposed images.

DESCRIPTION OF THE PRIOR ART

Regardless of the technique used, whether visual or one of the many sophisticated automated processes, the ease and accuracy with which patterns, and particularly fingerprints, can be compared depend on the clarity or level of contrast of the features making up the pattern or print images. Without clear, sharp and highly contrasted features comparison is at best difficult, time consuming and subject to a high degree of potential error. This is particularly so in the case of fingerprint comparison.

The various ink and dry-process fingerprinting techniques are intended to enhance the clarity and contrast between the ridges and valleys forming the characteristic print pattern. When the finger is viewed directly the clarity and contrast are poor.

A technique frequently used for enhancing the print pattern optically employs the principle of frustrated internal reflection within a prism. Certain undesirable features associated with this approach, however, make it difficult to work with. As viewed through one of the sides of the prism, the reflecting surface appears tilted and distorted and contains astigmatic aberrations. Additionally, as soon as the finger touches the glass surface of the prism, the oils in the skin leave a latent image which frustrate the internal reflection of the prism. This latent image can and does convolve with the actual ridge and valley pattern to cause distortion or blurring of the transmitted image.

The effects of such tilting and distortion can be corrected with elaborate off-axis optics. The astigmatic effects are much more difficult, if not impossible, to correct. By the same token, careful cleaning of the glass surface and cleansing of the finger to remove the oily deposit just prior to its application to the prism can reduce considerably the deleterious effects of latent image formation. Regardless of the corrective measures and precautions taken, the direct viewing technique requires that the finger be held absolutely immobile while it is in contact with the glass surface and throughout the comparison process.

By and large the various prior art attempts to resolve these problems in our judgment have been too complex and restrictive to be of practical value. The subject invention effectively eliminates all of these problems while providing print images of the highest quality and contrast by a far simpler method and means.

SUMMARY OF THE INVENTION

In our invention we have utilized the combined effects of the phenomena of scattering and light polarization to enhance a print image imposed in relief on the surface of a smooth, clear gel.

Essentially the method involves impressing the fingerprint pattern on the clear plane surface of a transparent pressure-sensitive film or tape. Contact with the ridges and grooves of the finger causes a relatively severe disturbance of the optical quality of the surface. This technique provides means for retaining a permanent record of the print for future use. By providing an elongated pressure-sensitive tape and means for advancing it to expose successive clear portions, a number of print images may be made and retained in a single roll.

It is well known that if a transparent print is illuminated by collimated light those areas where "positive" features of the print exist will scatter light out of the optical path, leaving a darker visible image. This image is similar to that obtained with a normal ink print in which the ridges are black and the valleys are clear.

In our enhancement method we polarize the collimated illumination before passing it through the image impressed on the gel surface. Areas where portions of the print disturb the surface rotate the plane of polarization to some extent and, if sufficient scattering exists, de-polarize some of the light entirely. We direct the light emitted from the transparency through a second polarizing element oriented so as to pass the original polarized illumination. In the areas in which the polarization of the original illumination has been disturbed, the image already darkened by light scattering is further darkened through polarization filtering. The total effect is one of substantial enhancement of the quality and contrast of the image.

The apparatus contemplated by the subject invention is intended primarily to be embodied in a module which can be adapted for use as a component in the fingerprint comparator described in our aforementioned co-pending application or in substantially any automated comparator system requiring a clear, high-contrast print image for analysis and comparison.

In one embodiment the device utilizes single transparencies of individual fingerprints. In another, a transport mechanism is provided for use with a tape strip on which a succession of prints may be impressed. In both embodiments an internally reflecting prism is utilized to allow the device to be packaged as a compact unit.

As mentioned in our co-pending parent application, the success of our fingerprint comparator is attributable to a great extent to the fact that the projected image to be compared with the fingerprint exempler is subjected to apodizing prior to the superimposition of the two images. Fortuitiously, the necessary apodization is inherent in the method and apparatus of the subject invention. This and other features and advantages of the invention will become apparent from a reading of the following description of several preferred embodiments as illustrated in the appended drawings.

BRIEF DESCRIPTION OF THE DRAWINGS

In the drawings:

FIG. 4 is a perspective view illustrating the principal structural elements of the fingerprint enchancing module shown in FIG. 1.

Wherever practicable the same numeral is used to identify identical or functionally similar components in the several figures.

DESCRIPTION OF THE PREFERRED EMBODIMENTS

The parent application discloses a method and means for automatically comparing two fingerprints, either opaque or transparent. The subject invention describes an adaptation which allows the direct comparison of the ridge pattern itself to a print exemplar, using the method and means of the parent application.

Figure 1:
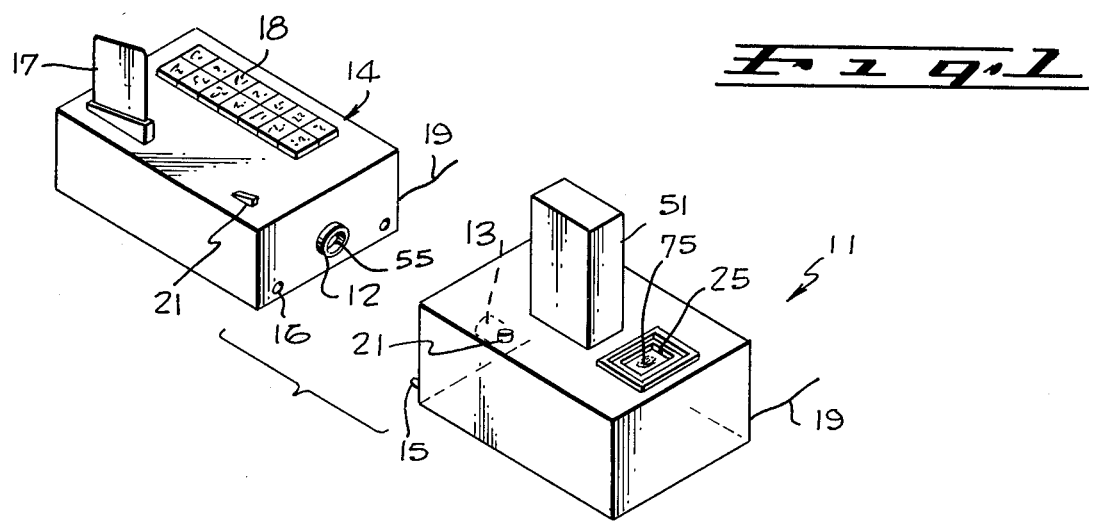
FIG. 1 is an exploded perspective view illustrating a fingerprint comparator incorporating a "live" print enhancing module embodying the subject invention.

Referring to FIG. 1, the preferred embodiment of the subject invention is incorporated in an image enhancing module 11 adapted to be mounted by conventional means such as an interlocking collar 12 and sleeve 13 to a comparator module 14 containing the image projection, apodizing and scanning mechanisms described in the parent application. Locating pins 15 and pin receivers 16 may be provided to permit accurate alignment of the two modules. As previously described, comparator module 14 is adapted to receive a fingerprint exemplar 17 which may take a variety of convenient forms, and additionally may be provided with a set of input keys 18 by means of which the elements of a transaction may be introduced into the system for appropriate annotation.

The two modules may be separately powered by means of individual electric cords 19, or may be provided with suitable conventional interconnecting means to operate on a single cord from one of the units. Likewise each of the units may be provided with an independent activating switch 21, or the two may be coupled so as to be activated by a single switch. As will be noted, image enhancing module 11 may be adapted for use with individual image receiving transparencies or strip tapes having multiple image recording capacity, or both. The embodiment illustrated in FIGS. 1 and 4 is of the latter type with the roll tape exposed through a window 25 at the top of the module casing.

Figure 2:
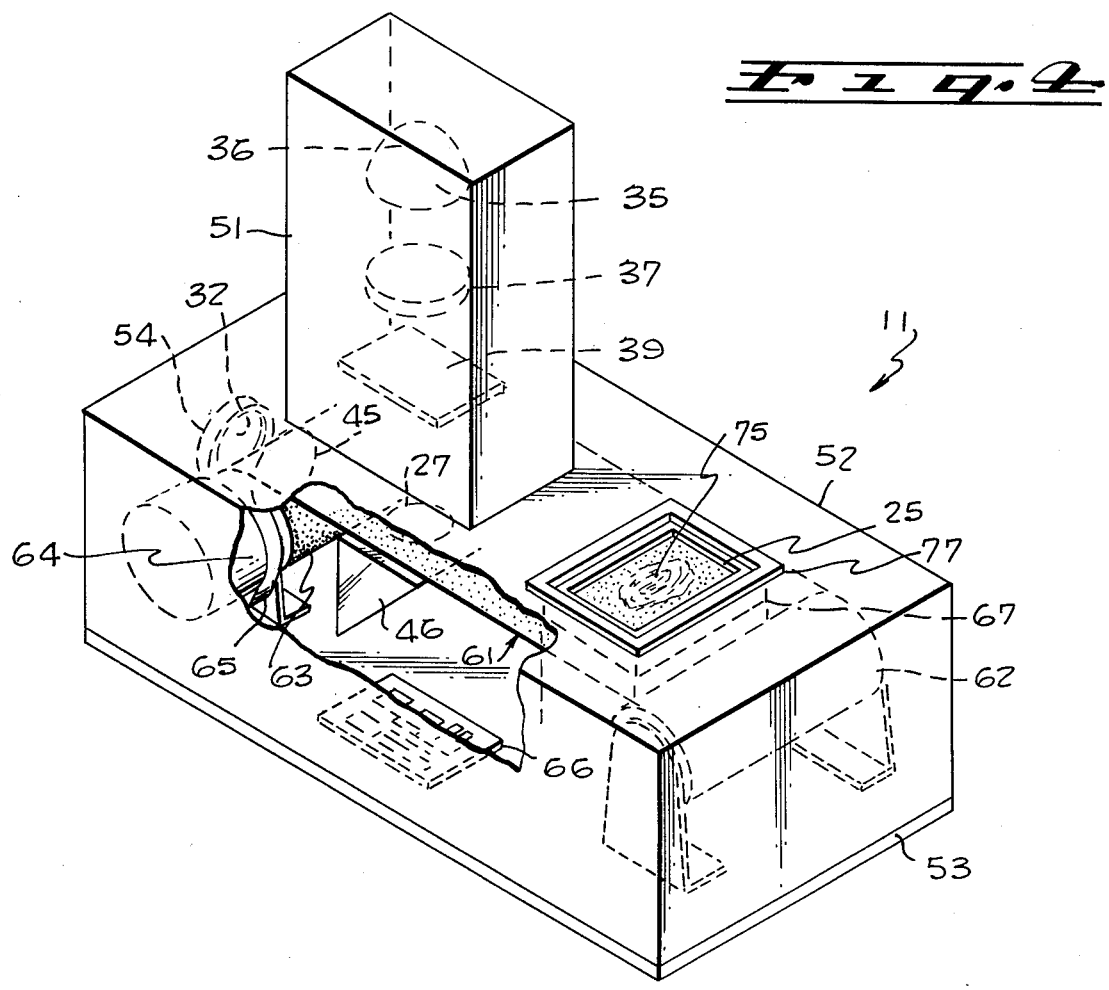
FIG. 2 is a diagrammatic view illustrating the optical principle employed in the subject invention for converting a faint translucent object into a high-contrast image.
Figure 2:
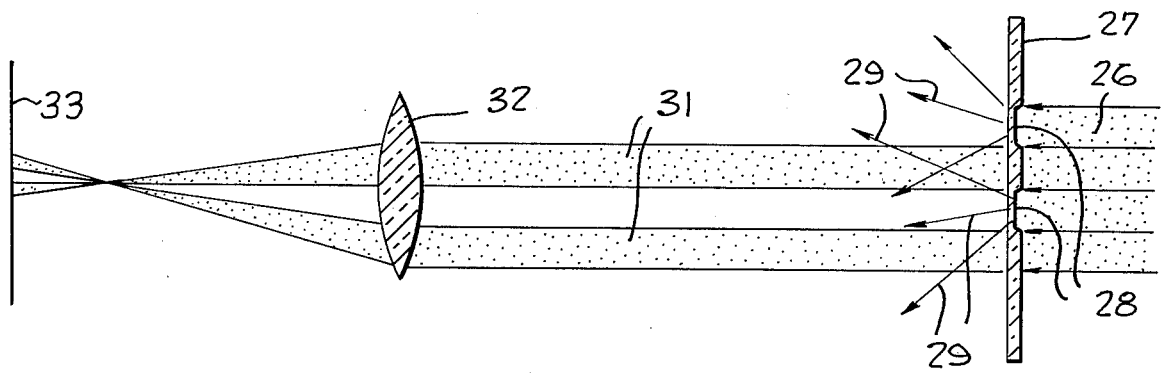

The principle of image enhancement by light scattering is illustrated in FIG. 2. When a beam of collimated light 26 passes through a transparent object plane 27 containing surface distortions such as indentations 28, a portion of the beam 26 is scattered by the distorted areas in more or less random rays 29. The remaining portions 31 of the original collimated beam 26 represent a much enhanced image of the distortion pattern. By passing the enhanced beam 31 through an imaging lens 32, a high-contrast image reproduction may be focused in an image plane 33 for subsequent utilization as, for example, in the comparator of the parent application. In the subject application the object plane 27 is the smooth, flat surface of a pressure sensitive gel, and the light scattering areas 28 are the distortions formed by the impression in that surface of the lands and grooves which form the indentifiable features of a "live" fingerprint.

Figure 3:
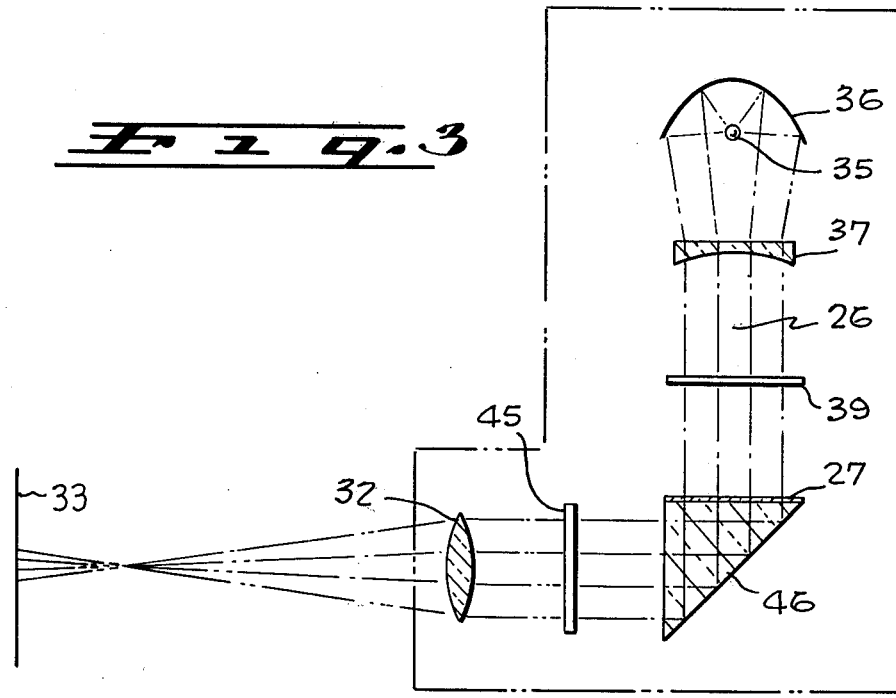
FIG. 3 is a schematic view illustrating the illumination and image projection techniques utilized in a preferred embodiment of the subject invention for imaging latent fingerprints.

FIG. 3 illustrates the method and means by which the high-contrast image formed by the application of the light-scattering principle is further enhanced and processed.

As shown, a light source, such as lamp 35, is provided with an elliptical dichroic reflector 36 which serves both to concentrate the illumination of lamp 35 on collimating lens 37 and to dissipate a substantial amount of the heat generated by lamp 35 without need to resort to elaborate external cooling means. Lens 37 collimates the illumination received from lamp 35 and directs the highly collimated beam 26 through illumination polarizer 39. Polarizer 39 may be a conventional polarizing filter having an axis of polarization transverse to the optical axis of beam 26.

The transparent, or perhaps more properly, partially translucent, print forming the distorted object plane 27 is positioned in the optical beam path. An image polarization analyzer 45 having its axis of polarization oriented in registry with the axis of polarization of polarizer 39 is positioned across the light beam path "downstream" from object print 27. As in FIG. 2, an imaging lens 32 serves to focus the beam on an image plane 33.

It will be noted that this optical system could be constructed with all of its elements arranged along a single linear axis. For convenience, however, in its preferred embodiment the system employs the right angle prism 46 interposed between object plane 27 and image polarization analyzer 45. This arrangement lends itself particularly well to the modular construction illustrated in FIGS. 1 and 4.

In addition to scattering the collimated light passing through them as mentioned previously, the disturbed portions of the object plane representing the fingerprint features cause a more or less random rotational displacement of the polarized wave front and, if sufficient scattering exists, may even de-polarize the light passing through these areas, entirely. Image polarization analyzer 45 serves as a filter to remove the portions of the polarized collimated beam 26 which are so affected, and thereby further enhances the image projected in image plane 33. The overall effect of the combined scattering and polarization filtering is to produce an image having a contrast pattern similar to that obtained with a conventional ink transfer, wherein the ridges of the original "live" print are black and the valleys are clear.

FIG. 4 depicts the system illustrated in FIG. 3 as embodied in the image enhancing module 11. Lamp 35, dichroic reflector 36, collimating lens 37 and illumination polarizer 39 are contained in a tower 51 mounted atop the casing 52 of the module 11. Casing 52, in turn, is mounted securely to a rigid base 53 which furnishes support for the entire structure. Imaging lens 32 is mounted in port 54 in the end wall of casing 52 in registry with a similar port 55 in the adjacent end wall of module 14, and prism 46 is positioned on base 53 to direct the collimated polarized beam from lamp 35 through the two ports 54, 55.

A roll of pressure sensitive tape 61 is removeably mounted on spool 62 and passes under window 25 and tower 51 to take-up spool 63. Motor 64 operates through speed reduction gear train 65 to drive spool 63 and thereby advance the tape 61 by the distance between window 25 and the optical path of the downwardly directed collimated light beam on activation of a switch 21. The electrical circuitry required for the operation of the module 11 is conveniently provided by one or more printed circuit boards 66 and their associated components.

A slightly resilient pad 67 is rigidly positioned beneath window 25 in contact with the underside of tape 61.

Figure 5:
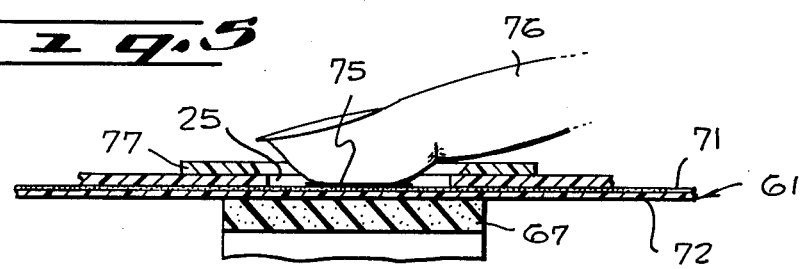
FIG. 5 is a fragmentary sectional view illustrating the operation of the module of FIG. 4 to form a transparency of a "live" fingerprint.

The method of affixing a "live" print to tape 61 is most clearly illustrated in FIG. 5. In actual use, conventional adhesive tape or book mending tape, such as "Scotch" brand, "Mylar" base tapes manufactured and sold by Minnesota Mining and Manufacturing Company, have served quite satisfactorily as roll tape 61. It will be understood, however, that the pressure sensitive surface layer 71 of tape 61 may be comprised of any suitable clear transparent gel material. Because of their commercial availability, the thermoplastic synthetic resin adhesives such as polyvinyl acetate, polyvinyl butyral, polyvinyl alcohol, the polystyrene resins, the acrylic and methacrylic acid ester resins, and various other synthetic resins such as polyisobutylene, polyamides, coumarone-indene products, and silicones, and the like, suggest themselves for the intended purpose. Some of these must be applied to a tape base 72, while others may be treated to provide a unitary tape having the desired pressure sensitive surface character.

Whatever the composition of the tape 61, when a "live" print 75 is to be taken for comparison with an exemplar 17, the finger 76 is brought into contact with the pressure sensitive surface of tape 61 through the open window 25 in the top of casing 52. A raised frame 77 may be provided adjacent window 25 to assist in locating the finger 76 in the window 25. Pad 67 below the tape 61 insures that only light contact is required between finger 76 and the surface 71 of the tape 61 to impress the features of print 75 in the surface. Preferably the gel selected for the surface 71 of tape 61 is one which leaves no residue on the finger 76, so there is no need to furnish cleaning material as there is when ink or one of the numerous other print reproduction solutions is used to form the object print.

Once the object print is formed in the surface of the tape 61, it constitutes a long-lasting record. With some of the aforementioned pressure sensitive materials this record may be considered substantially permanent.

If a greater degree of permanence than is afforded by the roll tape 61 is desired, the portion of the tape 61 bearing the print may be cut from the roll and mounted in a separate carrier for special treatment and isolated storage.

To introduce the object print into the comparator 14, switch 21 is activated, thereby advancing the print from its position in window 25 to a viewing position at the foot of tower 51. The electronic circuitry associated with the module 11 is programmed to actuate the lamp 35 when the object print is in the viewing position, and to keep it lit until the comparator 14 has completed its scanning operation as described in the parent application.

If it is desired to use the subject invention with individual transparencies containing the "live" object print, the window 25 may be adapted to allow the transparency to be inserted and attached to the surface of the tape 61, which can then act as a conveyor belt, or this mechanism may be eliminated entirely and the tower 51 hinged to be swung out of the way to permit the individual transparency to be positioned over prism 46 in the optical path.

It will be understood from the foregoing that the particular structures and embodiments described herein have been selected for illustrative purposes, and not by way of limitation on the scope of the invention as it is defined in the following claims.

What is claimed is:
1. A method for enhancing fingerprints comprising the steps of:
    impressing the features of a fingerprint in the surface of a transparent pressure sensitive gel;
    passing a collimated beam of polarized light through said gel;
    directing the portion of said light beam emitted by said gel through a polarized light filter; and
    projecting the portion of said light beam emitted by said filter to produce an illuminated image of said fingerprint in an image plane.
2. The method defined by claim 1, wherein said gel is supported by a carrier.
3. The method defined in claim 2, wherein said gel is a transparent wafer mounted to said carrier.
4. The method defined by claim 2, wherein:
    said carrier comprises an inelastic sheet of transparent material; and
    said gel is applied in a thin layer to the surface of said sheet.
5. The method defined by claim 4, wherein said gel comprises a thermoplastic adhesive.
6. The method defined by claim 5, wherein said sheet is an elongated strip.
7. The method defined by claim 6, wherein said strip is mounted to transport means for controlled movement across said light beam.
8. The method defined by claim 7, comprising the further steps of:
    impressing the features of a plurality of fingerprints in the surface of said gel at locations spaced along the length of said strip; and
    activating said transport means to selectively position said locations in said light beam.
9. The method defined by claim 8, wherein said gel and carrier are a pressure sensitive strip of cellophane adhesive tape.
10. A device for enhancing fingerprints comprising:
    a light source;
    means associated with said light source collimating light from said source and projecting said collimated light in an intense light beam;
    first polarizing means associated with said light source positioned across said light beam and oriented to polarize said light along an axis of polarization;
    a transparency comprising a transparent pressure sensitive gel adapted to retain an impression of the features of a fingerprint in the surface thereof;
    support means associated with said light source supporting said transparency in the path of said polarized light beam;
    second polarizing means associated with said light source positioned in said light beam on the side of said transparency remote from said first polarizing means and oriented with its axis of polarization aligned with that of said first polarizing means; and
    projection means associated with said light source projecting the portion of said light beam emitted by said second polarizing means to produce an illuminated image of said print in an image plane.

11. The fingerprint enhancing device defined by claim 10, wherein:
    said transparency comprises a strip of transparent pressure sensitive adhesive tape;
    said light source, collimating means, first polarizing means, support means, second polarizing means, and projecting means are mounted to a common base;
    a pad is mounted to said base, laterally spaced from said light beam and positioned subjacent to said tape strip to provide an unyielding abutment for said strip whereby the features of a print may be impressed in the surface of said tape by the application of pressure against the side of said tape opposite said pad; and
    said support means further comprises transport means controllably moving portions of said strip from a first position adjacent said path to a second position in the path of said light beam.

12. The fingerprint enhancing device defined by claim 11, wherein said transport means comprises:
    a pair of spools mounted to said base; and
    means controllably driving one of said spools.

* * * * *